United States Patent
Ehrhardt et al.

(10) Patent No.: US 7,300,767 B2
(45) Date of Patent: Nov. 27, 2007

(54) ASPARTATE CARBAMYLTRANSFERASE AS HERBICIDAL TARGET

(75) Inventors: Thomas Ehrhardt, Speyer (DE); Jens Lerchl, Ladenburg (DE); Marc Stitt Nigel, Edingen-Neckarhausen (DE); Rita Zrenner, Ladenburg (DE); Tina Maria Ritter, Dilsberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 353 days.

(21) Appl. No.: 10/204,836

(22) PCT Filed: Mar. 1, 2001

(86) PCT No.: PCT/EP01/02284

§ 371 (c)(1),
(2), (4) Date: Aug. 27, 2002

(87) PCT Pub. No.: WO01/64900

PCT Pub. Date: Sep. 7, 2001

(65) Prior Publication Data

US 2003/0148311 A1    Aug. 7, 2003

(30) Foreign Application Priority Data

Mar. 2, 2000    (DE) ................. 100 09 937

(51) Int. Cl.
*C12Q 1/48* (2006.01)
*C12N 9/10* (2006.01)
*C07H 21/04* (2006.01)

(52) U.S. Cl. .............. 435/15; 435/193; 536/23.2

(58) Field of Classification Search ............ 435/15, 435/193; 536/23.2
See application file for complete search history.

(56) References Cited

OTHER PUBLICATIONS

Guo et al. (Jun. 22, 2004) PNAS, vol. 101, No. 25, pp. 9205-9210.*
Hoefgen et al., Plant Physiol(1995) 107:469-477.
Overduin et al., Plant Physiol. vol. 105, 1994, 43-48.
Williamson et al., Plant Physiol., (1994)105:377-384.
Acaster et al., Carbamoyltransferase reactions . . . analogue inhibitors. J. Exp Botany. 40: 1121-1126, 1989.
Lovatt et al. Aspartate carbamyl . . . early-prolific-straightneck. Plant Phys. 75: 511-515, 1984.
Williamson et al. Molecular cloning . . . transcarbamoylase in pea (*Pisum sativum* L.). Plant Phys. 105: 377-388, 1993.

* cited by examiner

*Primary Examiner*—Elizabeth Slobodyansky
(74) *Attorney, Agent, or Firm*—Novak Druce & Quigg, LLP (57) ABSTRACT

The present invention relates to the use of DNA sequences of plant origin encoding a polypeptide with aspartate carbamyltransferase (E.C. 2.1.3.2) activity for generating an assay system for finding aspartate carbamyltransferase inhibitors. For the first time, it was shown, with the aid of antisense technology, that aspartate carbamyltransferase constitutes a herbicidal target.

4 Claims, 3 Drawing Sheets

ASPARTATE CARBAMYLTRANSFERASE AS HERBICIDAL TARGET

The present invention relates to the identification of plant aspartate carbamoyltransferase (E.C. 2.1.3.2) as novel target for herbicidal active ingredients. The present invention furthermore relates to the use of the DNA sequence SEQ-ID No. 1 or SEQ-ID No. 3 or SEQ-ID No. 5 or parts or derivatives encoding a plant polypeptide with aspartate carbamoyltransferase activity for generating an assay system for identifying plant aspartate carbamoyltransferase inhibitors. The invention also relates to a method or an assay system for finding substances which inhibit the activity of plant aspartate carbamoyltransferase and to plant aspartate carbamoyltransferase inhibitors identified using these methods or this assay system.

Plants are capable of synthesizing their cell components from carbon dioxide, water and inorganic salts.

This process is only possible by exploiting biochemical reactions for synthesizing organic substances. Nucleotides are synthesized de novo in plants. Being components of the nucleic acids, they are particularly important. Covalently bound, nucleotides activate carbohydrates for polysaccharide biosynthesis. They furthermore activate head groups for lipid biosynthesis. Nucleotides are involved in virtually all metabolic pathways. Nucleoside triphosphates, especially ATP, drive most of the energy-requiring reactions of the cell. Adenine nucleotides are additionally also found as components in essential factors such as coenzyme A and nicotinamide and flavin coenzymes, which are involved in a large number of cellular reactions. The coupled hydrolysis of guanosin-5'-triphosphate (GTP) defines a direction of reaction for various cellular processes such as protein translation, assembly of microtubuli, vesicular transport, signal transduction and cell division. Furthermore, nucleotides constitute the starting metabolites for the biosynthesis of methylxanthins such as caffeine and theobromine in the plant families of the Rubiaceae and Theaceae.

Since plants depend on an effective nucleotide metabolism, it can be assumed that enzymes which are involved in nucleotide biosynthesis are suitable as target protein (target) for herbicides. Thus, there have already been described active ingredients which inhibit de novo purin biosynthesis in plants. An example which may be mentioned is the natural substance hydanthocidin, which, after phosphorylation in planta inhibits adenylosuccinate synthetase (ASS) (Siehl et al., Plant Physiol. 110(1996), 753-758).

Both the enzyme reactions of the de novo purin biosynthesis and the enzyme reaction of the de novo pyrimidine biosynthesis are important for regulating the nucleotide metabolism. One of these enzymes is aspartate carbamoyltransferase (ATCase). In the second step of pyrimidine biosynthesis. ATCase catalyzes the linking of carbamoyl phosphate and aspartate to give carbamoyl aspartate, the substrate of dihydroorotase:

Carbamoyl phosphate is also the substrate of ornithin carbamoyltransferase in arginine biosynthesis. In plants and many other eukaryotes and prokaryotes, ATCase is subjected to allosteric feedback regulation by pyrimidine nucleotides. UMP and UDP have a more potent inhibitory action on zucchini ATCase than CMP and CDP (Lovatt and Cheng, Plant Physiol. 75(1984), 511-515). In Saccharomyces cerevisiae, the URA2 gene encodes a fusion protein with ATCase and carbamoyl phosphate synthetase activity (CPS). In higher eukaryotes, ATCase is a component of a trifunctional protein (CAD) which, in addition to ATCase and CPS, also comprises dihydroorotase. In *E. coli*, ATCase is present as a heteromeric complex of three catalytic and three regulatory subunits. A regulatory subunit has not been found for plant ATCase.

Plant ATCase genes were first isolated via functional complementation from *E. coli* (Williamson and Slocum, Plant Physiol. 105(1994), 377-384) and *Saccharomyces cerevisiae* pyrB mutants (Nasr et al., Mol. Gen. Genet. 244(1994), 23-32). In the meantime, ATCase genes from various plant species such as *Arabidopsis thaliana* (AB024036), *Plsum sativum* (M96981, U05293, L15798), *Lycopersicon esculentum* (X74072), *Oryza sativa* (C27734) and *Glycine max* (AW132309) can be found in the databases. Three ATCase isoforms were isolated from pea. At least one of the isoforms can be expressed functionally in *E. coli* (Williamson and Slocum, Plant Physiol. 105(1994), 377-384).

The ATCase activity in plants was detected predominantly in chloroplasts (Shibata et al., Plant Physiol. 80(1986), 126-129). The substrate analog N-(phosphonacetyl)-L-aspartate (PALA) is a potent ATCase inhibitor from pro- and eukaryotes and has an antimicrobial action.

Proof of the suitability of an enzyme as target for herbicides can be demonstrated by reducing the enzyme activity in transgenic plants, for example by means of antisense technology. If introducing an antisense DNA for a particular gene into a plant causes reduced growth, this suggest that the enzyme, whose activity has been reduced, is suitable as site of action for herbicidal active ingredients. For example, antisense inhibition of acetolactate synthase (ALS) in transgenic potato plants leads to comparable phenotype, does the treatment of control plants with ALS-inhibiting herbicides (Höfgen et al., Plant Physiology 107(1995), 469-477).

It is an object of the present invention to confirm that aspartate carbamoyltransferase in plants is a suitable herbicidal target, and to generate an efficient and simple aspartate carbamoyltransferase assay system for carrying out inhibitor-enzyme binding studies.

We have found that this object is achieved by isolating DNA sequences which encode the plant enzyme aspartate carbamoyltransferase, generating antisense constructs of plant aspartate carbamoyltransferase and expressing it in plants, and functionally expressing plant aspartate carbamoyltransferase in bacterial or eukaryotic cells.

To achieve the object, a cDNA encoding plant aspartate carbamoyltransferase from potato and two partial cDNAs from *Physcomitrella patens* were isolated and sequenced, see Examples 1, 2.1 and 2.2, or sequence listings SEQ-ID No. 1, SEQ-ID No. 3 and SEQ-ID No. 5.

Potato plants which carry an antisense construct of aspartate carbamoyltransferase were characterized in greater detail. The plants show different degrees of growth retardation. The transgenic lines and the progeny from the $1^{st}$ and $2^{nd}$ generation showed a reduced growth in soil. An aspertate carbamoyltransferase RNA quantity which was reduced compared with wild-type plants was detected by Northern hybridization in plants with reduced growth, see Example 5.

Furthermore, a quantity of aspartate carbamoyltransferase activity which was reduced compared with wild-type plants was detected in the transgenic lines by measuring the enzyme activity. The expression level and the reduction in aspartate carbamoyltransferase activity correlate with the growth retardation. Even though it is highly likely that several isoforms of aspartate carbamoyltransferase occur in potato plants, it has been found, surprisingly, that the introduction of an aspartate carbamoyltransferase antisense construct results in a reduced growth of the plant. This clear connection identifies aspartate carbamoyltransferase for the first time unambiguously as suitable target protein (target) for herbicidal active ingredients.

The invention furthermore relates to methods for identifying plant aspartate carbamoyltransferase inhibitors by high-throughput methods. The invention therefore relates to the functional expression of plant aspartate carbamoyltransferase, in particular from potato and *Physcomitrella patens* aspartate carbamoyltransferase, in suitable expression systems and to the use of the resulting enzymes in an in-vitro assay system for measuring the aspartate carbamoyltransferase activity.

To be able to find efficient plant aspartate carbamoyltransferase inhibitors, it is necessary to provide suitable assay systems with which inhibitor-enzyme binding studies can be carried out. To this end, for example, the complete cDNA sequence of the aspartate carbamoyltransferase or suitable fragments of the cDNA sequence of the potato or *Physcomitrella patens* aspartate carbamoyltransferase are cloned into an expression vector (pQE, Qiagen) and overexpressed in *E. coli*.

Alternatively, however, it is possible to express the expression cassette comprising a DNA sequence, or DNA subsequence, of SEQ-ID No. 1, SEQ-ID No.3 or SEQ-ID No. 5 or derivatives of these sequences, for example in other bacteria, in yeasts, fungi, algae, plant cells, insect cells or mammalian cells.

The invention furthermore relates to the use of DNA sequences derived from SEQ-ID NO. 1, SEQ-ID NO.3 or SEQ-ID NO. 5 or which hybridize with one of these sequences and which encode a protein which has the bioactivity of an aspartate carbamoyltransferase.

The plant aspartate carbamoyltransferase protein which is expressed with the aid of an expression cassette is particularly suitable for finding inhibitors which are specific to aspartate carbamoyltransferase.

To this end, for example, the plant aspartate carbamoyltransferase can be employed in an enzyme assay in which the aspartate carbamoyltransferase activity is determined in the presence and absence of the active ingredient to be assayed. A comparison of the two activity determinations allows a qualitative and quantitative statement to be made on the inhibitory behavior of the active ingredient to be assayed, see Example 9.

The assay system according to the invention allows a multiplicity of chemicals to be tested rapidly and simply for herbicidal properties. Using this method, substances with a potent action can be selected specifically and reproducibly from among a large number of substances in order that further in-depth tests with which the skilled worker is familiar can be carried out subsequently with these substances.

The invention furthermore relates to a method for identifying potentially herbicidally active plant aspartate carbamoyltransferase inhibitors by closing the gene of a plant aspartate carbamoyltransferase, overexpressing it in a suitable expression cassette—for example in insect cells, disrupting the cells and employing the cell extract in an assay system for measuring the enzyme activity in the presence of low-molecular-weight chemicals, either directly or after concentration or isolation of the enzyme aspartate carbamoyltransferase.

The invention furthermore relates to a method for identifying herbicidally active substances which inhibit aspartate carbamoyltransferase activity in plants, which method comprises a) generating transgenic plants, plant tissues or plant cells which comprise an additional DNA sequence encoding an enzyme with aspartate carbamoyltransferase activity and which are capable of overexpressing an enzymatically active aspartate carbamoyltransferase;

b) applying a substance to transgenic plants, plant cells, plant tissue or plant parts and to untransformed plants, plant cells, plant tissue or plant parts;

c) determining the growth or the survival capacity of the transgenic and the untransformed plants, plant cells, plant tissue or plant parts after applying the chemical substance; and d) comparing the growth or the survival capacity of the transgenic and the untransformed plants, plant cells, plant tissue or plant parts after applying the chemical substance;

where suppression of the growth or the survival capacity of the untransformed plants, plant cells, plant tissue or plant parts without, however, greatly suppressing the growth or the survival capacity of the transgenic plants, plant cells, plant tissue or plant parts, confirms that the substance of b) is herbicidally active and inhibits the aspartate carbamoyltransferase enzyme activity in plants.

The invention furthermore relates to herbicidally active compounds which can be identified with the above-described assay systems.

Herbicidally active aspartate carbamoyltransferase inhibitors can be employed as defoliants, desiccants, haulm killers and, in particular, as herbicides. Weeds in the widest sense are to be understood as meaning all plants which grow in locations where they are undesired. Whether the active ingredients found with the aid of the assay system according to the invention act as total or selective herbicides depends, inter alia, on the quantity applied.

Herbicidally active aspartate carbamoyltransferase inhibitors can be used, for example, against the following weeds:

Dicotyledonous Weeds of the Genera

Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.

Monocotyledonous Weeds of the Genera

Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus, Apera.

The invention also relates to the use of expression cassettes whose sequence encodes a potato or *Physcomitrella patens* aspartate carbamoyltransferase or its functional equivalent to generate an assay system for finding herbicidally active compounds. The nucleic acid sequence can be, for example, a DNA or cDNA sequence.

Such expression cassettes furthermore comprises regulatory nucleic acid sequences which govern the expression of the coding sequence in the host cell. In accordance with a preferred embodiment, an expression cassette according to the invention encompasses upstream, i.e. at the 5' end of the coding sequence, a promoter, and downstream, i.e. at the 3' end, a polyadenylation signal and, if appropriate, other regulatory elements which are operatively linked to the coding sequence for the aspartate carbamoyltransferase gene, which lies in between. Operative linkage is to be understood as meaning the sequential arrangement of promoter, coding sequence, terminator and, if appropriate, other regulatory elements in such amounts that each of the regulatory elements can function as intended when the coding sequence is expressed.

An expression cassette of this type is generated by fusing a suitable promoter with a suitable aspartate carbamoyltransferase DNA sequence and a polyadenylation signal using customary recombination and cloning techniques such as described, for example, by T. Maniatis, E. F. Fritsch and J. Sambrook, Molecular Cloning: A Laboratory Manual, Cold Spring Harbor Laboratory, Cold Spring Harbor, N.Y. (1989) and by T. J. Silhavy, M. L. Berman and L. W. Enquist, Experiments with Gene Fusions, Cold Spring Harbor Laboratory, Cold Spring Harbor, N.Y. (1984) and by Ausubel, F. M. et al., Current Protocols in Molecular Biology, Greene Publishing Assoc. and Wiley-Interscience (1987).

The invention relates to the use also of functionally equivalent DNA sequences which encode an aspartate carbamoyltransferase gene and which show a sequence homology with the DNA sequence SEQ-ID NO. 1, SEQ-ID NO. 3 or SEQ-ID NO. 5 of 40 to 100%, based on the total length of the DNA sequence.

The invention preferably relates to the use of functionally equivalent DNA sequences which encode an aspartate carbamoyltransferase gene and which show a sequence homology with the DNA sequence SEQ-ID NO. 1, SEQ-ID NO.3 or SEQ-ID NO. 5 of 60 to 100%, based on the total length of the DNA sequence.

The invention particularly preferably relates to the use of functionally equivalent DNA sequences which encode an aspartate carbamoyltransferase gene and which show a sequence homology with the DNA sequence SEQ-ID NO. 1, SEQ-ID NO.3 or SEQ-ID NO. 5 of 80 to 100%, based on the total length of the DNA sequence.

Functionally equivalent sequences which encode an aspartate carbamoyltransferase gene are those sequences which retain the desired functions, despite a deviating nucleotide sequence. Functional equivalents thus encompass naturally occurring variants of the sequences described herein, but also artificial nucleotide sequences, for example those which have been obtained by chemical synthesis and which are adapted to suit the codon usage of a plant.

A functional equivalent is also to be understood as meaning in particular natural or artificial mutations of an originally isolated sequence which encodes an aspartate carbamoyltransferase and which continues to show the desired function. Mutations encompass substitutions, additions, deletions, exchanges or insertions of one or more nucleotide residues. Thus, the present invention for example also extends to the nucleotide sequences which are obtained by modifying this nucleotide sequence. The aim of such a modification can be, for example, the further delimitation of the encoding sequence contained therein or else, for example, the introduction of further restriction enzyme cleavage sites.

Functional equivalents are also those variants whose function is reduced or increased compared with the starting gene or gene fragment.

In addition, the expression cassette can also be employed for the transformation of bacteria, cyanobacteria, yeasts, filamentous fungi and algae, and eukaryotic cells (for example insect cells), with the aim of generating sufficient amounts of the enzyme aspartate carbamoyltransferase.

The invention furthermore relates to the use of a potato or *Physcomitrella patens* protein characterized by the amino acid sequence SEQ-ID NO. 2 or SEQ-ID NO.4 or SEQ-ID NO.6 or derivatives or parts of this protein with aspartate carbamoyltransferase activity for the generation of an assay system for finding herbicidally active compounds.

The invention also relates to the use of plant proteins with aspartate carbamoyltransferase activity with an amino acid sequence homology to the potato or *Physcomitrella patens* aspartate carbamoyltransferase with SEQ-ID No.2 or SEQ-ID NO.4 or SEQ-ID NO. 6 of 20-100% identity for generating an assay system for finding herbicidally active compounds.

Also preferred is the use of plant proteins with aspartate carbamoyltransferase activity with an amino acid sequence homology to the potato or *Physcomitrella patens* aspartate carbamoyltransferase with SEQ-ID No.2 or SEQ-ID NO.4 or SEQ-ID NO.6 or 50-100% identity for generating an assay system for finding herbicidally active compounds.

Especially preferred is the use of plant proteins with aspartate carbamoyltransferase activity with an amino acid sequence homology to the potato or *Physcomitrella patens* aspartate carbamoyltransferase with SEQ-ID No.2 or SEQ-ID NO.4 or SEQ-ID NO.6 of 80-100% identity for generating an assay system for finding herbicidally active compounds.

Also encompassed in accordance with the invention are the isoenzymes of aspartate carbamoyltransferase. Thus, the *Physcomitrella patens* genes with SEQ-ID NO. 3 and SEQ-ID NO. 5 encode two ATCase isoenzymes (SEQ-ID NOS.4 and 6) which are probably expressed during different developmental stages in moss.

Isoenzymes are understood as meaning isoforms of enzymes with the same or comparable substrate specificity and specificity of action, but which have a different primary structure.

Overexpression, in a plant, of the gene sequence SEQ-ID NO. 1, SEQ-ID NO. 3 or SEQ-ID NO. 5, which encodes an aspartate carbamoyltransferase, results in an increased resistance to aspartate carbamoyltransferase inhibitors. The transgenic plants generated thus are also subject matter of the invention.

Expressional efficacy of the recombinantly expressed aspartate carbamoyltransferase gene can be determined, for example, in vitro by shoot-meristem propagation or by a germination test. Moreover, the expression of the aspartate carbamoyltransferase gene which has been altered in terms of type and level, and its effect on the resistance to aspartate carbamoyltransferase inhibitors, can be tested in greenhouse experiments using test plants.

The invention furthermore relates to transgenic plants, transformed with an expression cassette containing the DNA sequence SEQ-ID NO. 1, SEQ-ID NO.3 or SEQ-ID NO.5, which have been made tolerant to aspartate carbamoyltransferase inhibitors by additionally expressing the DNA sequence SEQ-ID NO. 1, SEQ-ID NO.3 or SEQ-ID NO. 5, and to transgenic cells, tissue, parts and propagation material of such plants. Especially preferred are transgenic crop plants such as, for example, barley, wheat, rye, maize, soya, rice, cotton, sugar beet, canola, sunflowers, flax, hemp, potatoes, tobacco, tomatoes, oilseed rape, alfalfa, lettuce and the various tree, nut and grapevine species, and also legumes.

Especially preferred sequences are those which ensure targeting into the apoplast, into plastids, the vacuole, the mitochondrium, the endoplasmatic reticulum (ER) or which, owing to the absence of suitable operative sequences, ensure that the product remains in the compartment of the formation, the cytosol (Kermode, Crit. Rev. Plant Sci. 15, 4 (1996), 285-423).

For example, the plant expression cassette can be introduced into the plant transformation vector pBinAR.

A suitable promoter of the expression cassette is, in principle, any promoter which is capable of governing the expression of foreign genes in plants. It is preferred to use, in particular, a plant promoter or promoter derived from a plant virus. Particularly preferred is the cauliflower mosaic virus CaMV 35S promoter (Franck et al., Cell 21 (1980), 285-294). This promoter contains different recognition sequences for transcriptional effectors which, in their totality, lead to permanent and constitutive expression of the gene which has been introduced (Benfey et al., EMBO J., 8 (1989), 2195-2202).

The expression cassette may also contain a chemically inducible promoter which allows expression of the exogenous aspartate carbamoyltransferase gene in the plant to be governed at a particular point in time. Such promoters which are described in the literature and which can be used are, inter alia, for example the PRPI promoter (Ward et al., Plant. Mol. Biol. 22 (1993), 361-366), a salicylic acid-inducible promoter (WO 95/19443), a benzenesulfonamide-inducible promoter (EP 388186), a tetracycline-inducible promoter (Gatz et al., Plant J. 2(1992), 397-404), an abscisic acid-inducible promoter (EP 0335528) or an ethanol- or cyclohexanone-inducible promoter (WO 93/21334).

Especially preferred promoters are furthermore those which ensure expression in tissues or plant parts in which the biosynthesis of purins or their precursors takes place. Promoters which ensure leaf-specific expression must be mentioned in particular. Promoters which must be mentioned are the potato cytosolic FBPase or the potato ST-LSI promoter (Stockhaus et al., EMBO J., 8 (1989) 2445-245).

A foreign protein can be expressed stably in the seeds of transgenic tobacco plants to an extent of 0.67% of the total soluble seed protein with the aid of a seed-specific promoter (Fiedler and Conrad, Bio/Technology 10 (1995), 1090-1094). The expression cassette according to the invention can therefore contain, for example, a seed-specific promoter (preferably the phaseolin promoter, the USP promoter or the LEB4 promoter), the LEB4 signal peptide, the gene to be expressed and an ER retention signal.

The inserted nucleotide sequence encoding an aspartate carbamoyltransferase can be produced synthetically or obtained naturally or contain a mixture of synthetic and natural DNA components. In general, synthetic nucleotide sequences are generated with codons which are preferred by plants. These codons which are preferred by plants can be determined from codons with the highest protein frequency expressed in the plant species of the greatest interest. When preparing an expression cassette, a variety of DNA fragments may be manipulated in order to obtain a nucleotide sequence which expediently reads in the correct direction and which is equipped with the correct reading frame. Adapters or linkers can be added to the fragments in order to link DNA fragments to each other.

Other suitable DNA sequences are artificial DNA sequences as long as they mediate the desired property of expressing the aspartate carbamoyltransferase gene as described above, for example. Such artificial DNA sequence can be determined, for example, by back-translating proteins which have aspartate carbamoyltransferase activity and which have been constructed by means of molecular modeling, or they can be determined by in-vitro selection. Especially suitable are coding DNA sequences which have been obtained by back-translating a polypeptide sequence in accordance with the host-plant-specific codon usage. The specific codon usage can be determined readily by a skilled worker familiar with plant genetics methods by means of computer evaluations of other known genes of the plant to be transformed.

Other suitable equivalent nucleic acid sequences which must be mentioned are sequences which encode fusion proteins, a component of the fusion protein being a plant aspartate carbamoyltransferase polypeptide or a functionally equivalent part thereof. The second part of the fusion protein can be, for example, another polypeptide with enzymatic activity or an antigenic polypeptide sequence with the aid of which detection of aspartate carbamoyltransferase expression is possible (for example myc-tag or his-tag). However, it is preferably a regulatory protein sequence such as, for example, a signal or transit peptide, which leads the aspartate carbamoyltransferase protein to the desired site of action.

The promoter and terminator regions should expediently be provided, in the direction of transcription, with a linker or polylinker containing one or more restriction sites for insertion of this sequence. As a rule, the linker has 1 to 10, in most cases 1 to 8, preferably 2 to 6, restriction sites. In general, the linker within the regulatory regions has a size of less than 100 bp, frequently less than 60 bp, but at least 5 bp. The promoter according to the invention may be native, or homologous, or else foreign, or heterologous, to the host plant. The expression cassette according to the invention, comprises, in the 5'-3' direction of transcription, the promoter according to the invention, any sequence and a region for transcriptional termination. Various termination regions can be exchanged for each other as desired.

Manipulations which provide suitable restriction cleavage sites or which eliminate the excess DNA or restriction cleavage sites may also be employed. In-vitro mutagenesis, primer repair, restriction or ligation may be used in cases where insertions, deletions or substitutions such as, for example, transitions and transversions, are suitable. Complementary ends of the fragments may be provided for ligation in the case of suitable manipulations, such as, for example, restriction, chewing-back of filling up overhangs for blunt ends.

Preferred polyadenylation signals are plant polyadenylation signals, preferably those which correspond essentially to Agrobacterium tumefaciens T-DNA polyadenylation signals, in particular those of gene 3 of the T-DNA (octopine synthase) of the Ti plasmid pTiACH5 (Gielen et al., EMBO J., 3 (1984), 835), or functional equivalents.

To transform a host plant with a DNA encoding an aspartate carbamoyltransferase, an expression cassette is incorporated, as insertion, into a recombinant vector whose vector DNA contains additional functional regulatory signals, for example sequences for replication or integration. Suitable vectors are described, inter alia, in "Methods in Plant Molecular Biology and Biotechnology" (CRC Press, Chapter 6/7, 71-119).

The transfer of foreign genes in to the genome of a plant is termed transformation. It exploits the above-described methods for transforming and regenerating plants from plant tissues or plant cells for transient or stable transformation. Suitable methods are the protoplast transformation by polyethylene glycol-induced DNA uptake, the biolistic approach using the gene gun, electroporation, incubation of dry embryos in DNA-containing solution, microinjection and Agrobacterium-mediated gene transfer. The abovementioned methods are described by, for example, B. Jenes et al., Techniques for Gene Transfer, in: Transgenic Plants, Vol. 1, Engineering and Utilization, edited by S. D. Kung and R. Wu, Academic Press (1993), 128-143 and Potrykus, Annu. Rev. Plant Physiol. Plant Molec. Biol. 42 (1991), 205-225. The construct to be expressed is preferably cloned into a vector which is suitable for the transformation of Agrobacterium tumefaciens, for example pBin19 (Bevan et al., Nucl. Acids Res. 12 (1984), 8711).

Agrobacteria transformed with an expression cassette can equally be used in a known manner for transforming plants, in particular crop plants such as cereals, maize, soya, rice, cotton, sugar beet, canola, sunflowers, flax, hemp, potatoes, tobacco, tomatoes, oilseed rape, alfalfa, lettuce and the various tree, nut and grapevine species, and also legumes, for example by bathing wounded leaves or leaf sections in an agrobacterial solution and subsequently growing them into suitable media.

The pyrimidine biosynthesis site is generally the leaf tissue, so that leaf-specific expression of the aspartate carbamoyltransferase gene makes sense. However, it is obvious that pyrimidine biosynthesis need not be limited to leaf tissue, but may also take place in a tissue-specific fashion in all other remaining parts of the plant, for example in fatty seeds.

In addition, a constitutive expression of the exogenous aspartate carbamoyltransferase gene is advantageous. On the other hand, however, inducible expression may also be desirable.

Using the recombination and cloning techniques cited above, the expression cassettes can be cloned into suitable vectors which allow them to be multiplied, for example in E. coli. Examples of suitable cloning vectors are pBR332, pUC series, M13mp series and pACYC184. Especially suitable are binary vectors, which are capable of replication both in E. coli and in agrobacteria.

The invention furthermore relates to the use of an expression cassette according to the invention for transforming plants, plant cells, plant tissues or plant parts. The preferred purpose of the use is to increase the aspartate carbamoyltransferase content in the plant.

Depending on the choice of promoter, expression may take place specifically in the leaves, in the seeds or in other parts of the plant. Such transgenic plants, their propagation material and their plant cells, plant tissue or plant parts are further subject matter of the present invention.

The invention will now be illustrated by the examples which follow, without being limited thereto.

Genetic engineering methods on which the use examples are based:

General Cloning Methods

Cloning methods as, for example, restriction cleavages, DNA isolation, agarose gel electrophoresis, purification of DNA fragments, transfer of nucleic acids to nitrocellulose and nylon membranes, linking DNA fragments, transformation of E. coli cells, bacterial cultures and the sequence analysis of recombinant DNA were carried out as described by Sambrook et al., Cold Spring Harbor Laboratory Press (1989); ISBN 0-87969-309-6. Agrobacterium tumefaciens was transformed by the method of Höfgen and Willmitzer (Nucl. Acid Res. 16(1988), 9877). Agrobacterial cultures were performed in YEB medium (Vervliet et al., Gen. Virol. 26(1975), 33).

Sequence Analysis of Recombinant DNA

Recombinant DNA molecules were sequenced using an ABI laser fluorescence DNA sequencer, using the method of Sanger (Sanger et al., Proc. Natl. Acad. Sci. USA, 74(1977), 5463-5467). Fragments resulting from a polymerase chain reaction were sequenced and verified to avoid polymerase errors in constructs to be expressed.

Analysis of Total RNA from Plant Tissues

Total RNA from plant tissues was isolated as described by Logemann et al., Anal. Biochem. 163(1987), 21. For the analysis, in each case 20 mg of RNA were separated in a formaldehyde-containing 1.5% strength agarose gel and transferred to Duralon UV membranes (Stratagene). To detect specific transcripts, digoxygenin-labeled strand-specific probes were prepared following the manufacturer's instructions (DIG RNA Labeling Kit SP6/T7, Roche Diagnostics) and used for hybridization (DIG EasyHyb, Roche Diagnostics). Then, the membranes were washed 3×20 minutes in wash buffer (2×SSC, 0.1% SDS) at 60° C. Detection was carried out using the Roche Diagnostics DIG detection system by luminescence and exposure to Hyperfilm ECL (Amersham) using CDP-Star as substrate.

Wester Blot Analysis

Using a pestle and mortar, leaf samples were comminuted in sample buffer at a ratio of 1:10 for SDS-polyacrylamide gel electrophoresis (Sambrook et al., 1989, Cold Spring Harbor Laboratory Press: ISBM 0-87969-309-6) and denatured for 10 minutes at 95° C. Equal extract quantities were separated by SDS-polyacrylamide gel electrophoresis (PAGE) and transferred to PVDF membranes. The membranes were incubated for 1 hour at room temperature in 5% strength Blocking solution (Blotto, BioRad). This was followed by the following incubations:

Antibody incubation: 1:2000 dilution of the antiserum for 1 hour at RT in 2.5% strength Blocking solution.

Washing: 1×briefly with TBS (20 mM Tris HCl and 500 mM NaCl pH 7.5), 1×15 minutes TBST (TBS with 0.1% (v/v) Tween 20), 1×15 minutes TBS.

Antibody incubation: Anti-rabbit IgG coupled with alkaline phosphatase (BioRad) in a 1:2000 dilution in 2.5% strength Blocking solution for 1 hour at RT.

Washing: 1×briefly with TBS (20 mM Tris HCl and 500 mM NaCl pH 7.5), 1×15 minutes Detection: Incubation in 100 mM Tris-HCl, pH 9.5; 100 mM NaCl; 5 mM $MgCl_2$ with BCIP (0.167 mg/ml) and NBT (0.333 mg/ml).

Unless otherwise specified, the chemicals used were obtained in analytical-grade quality from Fluka (Neu-Ulm), Merck (Darmstadt), Roth (Karlsruhe), Serva (Heidelberg) and Sigma (Deisenhofen). Solutions were made with purified, pyrogen-free water, termed $H_2O$ hereinbelow, from a Milli-Q water purification system (Millipore, Eschborn). Restriction endonucleases, DNA-modifying enzymes and molecular biology kits were obtained from AGS (Heidelberg), Amersham (Braunschweig), Biometra (Göttingen), Roche (Mannheim), Genomed (Bad Oeynnhausen), New England Biolabs (Schwallbach/Taunus), Novagen (Madison, Wis., USA), Perkin-Elmer (Weiterstadt), Pharmacia (Freiburg), Qiagen (Hilden) and Stratagene (Heidelberg). Unless otherwise specified, they were used in accordance with the manufacturer's instructions.

BRIEF DESCRIPTION OF THE DRAWINGS

FIG. 1: (A) Schematic representation of the expression vector pBlueskript SK comprising a cDNA encoding a potato ATCase (RBP3b) and promoters of the bacteriophages T3 or T7. Single recognition sites for restriction endonucleases are shown.

(B) Schematic representation of the plant transformation vector BinRBP3b comprising a cDNA encoding a potato ATCase (RBP3b) in antisense orientation in the vector pBinAR and the cauliflower mosaic virus (CaMV) 35S promoter and the Agrobacterium tumefaciens octopinesynthetase (OCS) terminator. Singular recognition sites for restriction endonucleases are shown.

EXAMPLE 1

Isolation of a cDNA Encoding a Functional Potato ATCase

A clone encoding a potato ATCase was isolated via functional complementation of an *E. coli* pyrB mutant CGSC#6852 of the *E. coli* Genetic Stock Center (RBP3b). Complementation was carried out by electrotransformation with $5*10^5$ cfu of a cDNA library in the vector plasmid pBS SK—. The lambda ZAPII library (Stratagene) which formed the base was prepared by standard protocols using EcoRI/NotI linkers. The RNA template for generating the cDNA library was isolated from potato sink leaves (smaller 1 cm, 10-week old greenhouse-grown potato plants).

The transformed bacteria were plated onto M9 minimal medium (Sambrook et al., 1989) which additionally contained methionine (20 mg/l), thiamine (100 mg/l), ampicillin (100 mg/l) and IPTG (2.5 mM). The plasmid of a complementing clone (termed pRBP3b) was isolated and sequenced. The cDNA encodes, on 1344 nucleotides, a protein of 412 amino acids (SEQ-ID NO. 1 and 2). A sequence comparison of the amino acid sequence with the pea ATCase (Genbank Accession No. M96981) suggests that RBP3b constitutes a full-length cDNA. Amino acid 36 probably constitutes the start methionine. The derived protein is 83.9% similar to the *Arabidopsis thaliana* ATCase. The similarity to *E. coli* and human ATCases in 63.0% and 65.6%, respectively. The nucleotide sequence shows 75.4% identity with the *Arabidopsis thaliana* gene, 54.4% identity with the *E. coli* gene and 66.4% identity with human cDNA.

EXAMPLE 2.1

Isolation of a cDNA Encoding an ATCase from Moss

Double-stranded cDNA was generated from *Physcomitrella patens* protonemal mRNA and used for generating a cDNA library in the vector pBluescript SKII (lambda ZAP II RI Library Construction Kit, Stratagene). Individual clones of this library were part-sequenced. The sequence of clone pp001057045r showed marked homology on the 3'-side to plant ATCase. Clone pp001057045r was sequenced in its entirety. On a partial cDNA of 617 base pairs, it encodes a polypeptide of 118 amino acids (SEQ-ID NO. 3 and 4). At amino acid level, pp001057045r shows 72.9% identity with the *Arabidopsis thaliana* ATCase and 49.1% identity with the *E. coli* ATCase. The nucleotide sequence shows 75.4% identity with the *Arabidopsis thaliana* gene and 54.8% identity with the *E. coli* and human genes.

EXAMPLE 2.2

Isolation of a cDNA Encoding a Further ATCase From Moss (Isoenzyme)

Double-stranded cDNA was generated from *Physcomitrella patens* gametophore mRNA and subtracted from *Physcomitrella patens* protonemal cDNA. The resulting cDNA was used for generating a plasmid cDNA library in the vector pUC19 (Roche, Mannheim). Individual clones of this library were part-sequenced. The sequence of the clone c_pp015013185r showed marked homology on the 3'-side to plant ATCase. Clone c_pp015013185r was sequenced in its entirety. The partial cDNA of 1251 base pairs encodes a polypeptide of 310 amino acids (SEQ-ID NO. 5 and 6). The nucleotide sequence of c_pp015013185r has 69% identity with the *Arabidopsis thaliana* gene (Genbank Accession No. X71843). The protein encoded by c_pp015013185r has 79.7% identity with *Arabidopsis* ATCase. The identity with clone pp001057045r from moss is 74.5% at the nucleotide sequence level and 81.9% at the amino acid sequence level. These two clones from moss encode two ATCase isoenzymes which are probably expressed during different developmental stages in moss.

EXAMPLE 3

Construction of a Plant Transformation Vector

Figure 1:
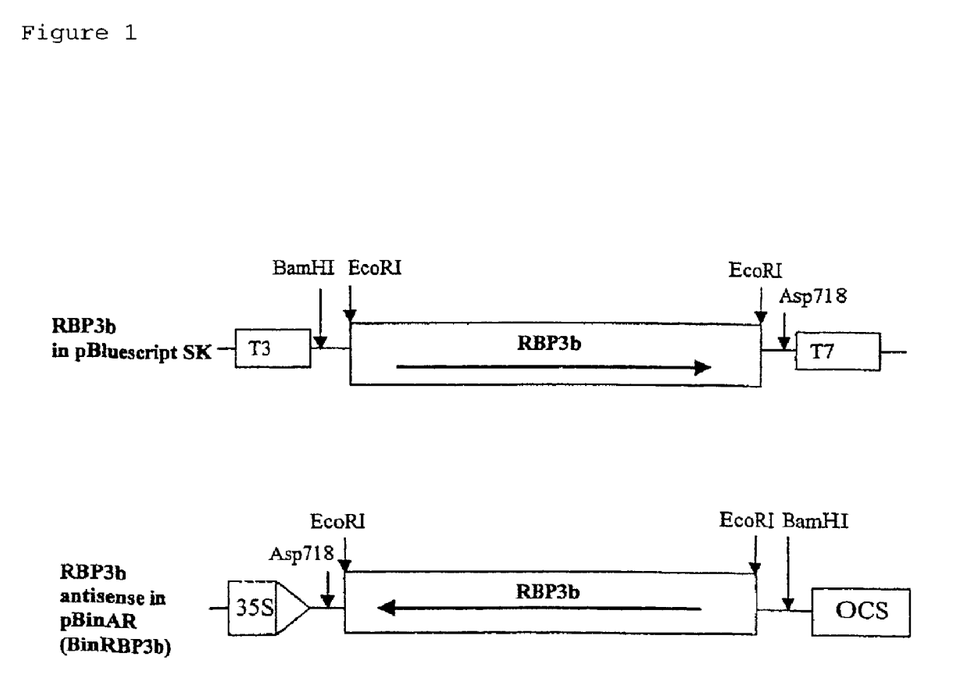

A 1494 bp RBP3b cDNA fragment containing the RBP3b cDNA was obtained by cleavage with Asp718 and BamHI and ligated into vector BinAR (Höfgen and Willmitzer, Plant Science 66 (1990), 221-230), which had been cleaved in the same manner. The resulting construct BinRBP3b contains the RBP3b cDNA in antisense orientation relative to the cauliflower mosaic virus 35S promoter (FIG. 1).

EXAMPLE 4

Generation of Transgenic Potato Plants

To transform potato plants (cv. Desirée), the construct BinRBP3b was first transformed into *Agrobacterium tumefaciens* C58C1:pGV2260 (Deblaere et al., Nucl. Acids. Res. 13(1984), 4777-4788). To transform potato by the method of Rocha-Sosa et al., EMBO J., 8(1988), 23-29, a 1:50 dilution of an overnight culture of a positively transformed agrobacterial colony in Murashige-skoog medium (Physiol. Plant. 15(1962), 473) was used. Leaf disks of sterile plants (approx. 1 cm² each) were incubated for 5-10 minutes with a 1:50 agrobacterial dilution in a Petri dish. This was followed by 2 days' incubation in the dark at 20° C. on MS medium. Culturing was then continued in a 16-hour-light/8-hour-dark photoperiod. Transferrals to MS medium with 500 mg/l claforan (cefotaxime-sodium), 50 mg/l kanamycin and plant hormones (Rocha-Sosa et al., EMBO J., 8(1989), 23-29) and 16 g/l glucose were carried out weekly in order to induce shoots. Growing shoots were transferred to MS medium with 2% sucrose, 250 mg/l claforan and 0.8% Bacto agar.

Regenerated shoots were obtained on MS medium with 20 g/l sucrose and with kanamycin and claforan, transferred into soil once they had rooted and, after they had been grown for 2 weeks in a controlled-environment cabinet in a 16-hour-light/8-hour-dark photoperiod at a relative atmospheric humidity of 50% examined for expression of the foreign gene and for altered metabolite contents and phenotypic growth characteristics. Altered nucleotide contents can be determined, for example, by the method of Stitt et al., FEBS Letters, 145(1982), 217-222.

EXAMPLE 5

Northern Blot Analysis of the Transgenic Plants

The plants transformed with the BinRBP3b antisense construct (see FIG. 5) were analyzed by means of Northern blot analyses using a strand-specific probe for detecting the ATCase mRNA. To construct the strand-specific probe, pRBP3b was cleaved with BamHI. The labeling reaction was carried out with the aid of T7 RNA polymerase (DIG RNA Labeling Kit, Roche Diagnostics). It emerged that the ATCase mRNA quantity in lines 8, 17, 19, 44, 51, 53 and 60 was reduced by different degrees.

EXAMPLE 6

Overexpression of a Potato ATCase Fragment in *E coli*, and Generation Of Antibodies For the purposes of overexpression in *E. coli*, a 1272 bp fragment of the RBP3b cDNA was obtained by cleavage with BamHI and HindIII and ligated into vector pQE-9 (Qiagen) which had been cleaved in the same manner. The resulting construct QERBP3b encodes the entire ATCase polypeptide from RBP3b, whose N-terminus is fused to a hexahistidine anchor and 52 other amino acids encoded by DNA linker sequences and 5'-untranslated sequences. QERBP3b was transformed into *E. coli* XL1-blue (Stratagene). IPTG-induced day cultures were harvested by centrifugation. The cell pellets were disrupted under denaturing conditions following the manufacturer's instructions, and the ATCase protein was purified by nickel affinity chromatography ("Qia-Express-Kit", Qiagen). In this manner, the ATCase was purified to >95%. The protein was used for generating antisera in rabbits following customary protocols (for example commissioned from Eurogentec).

EXAMPLE 7

Detection of Potato ATCase in Leaf Tissues

Figure 2:
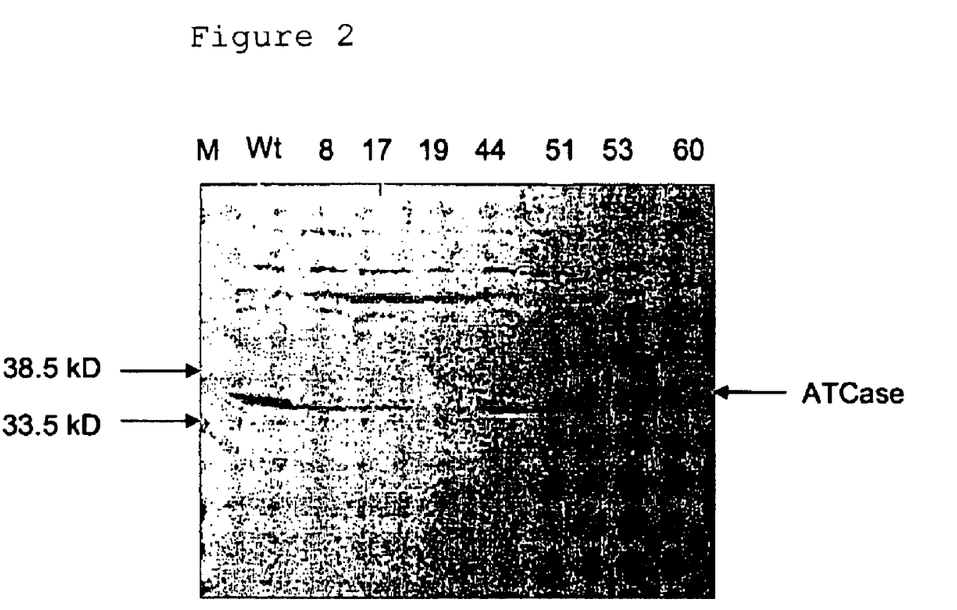
FIG. 2: Western blot analysis for detecting the potato ATCase in leaf tissue. The use of a molecular weight marker (M) and extracts of the transgenic plant lines 8, 17, 19, 44, 51, 53 and 60 in comparison with the wild type (WT) for hybridization with ATCase antiserum are shown.

In Western blot experiments, the ATCase antiserum specifically recognizes the potato polypeptide in the form of a band at a molecular weight of approx. 36 kD. The antiserum allowed transgenic plants which carry an ATCase antisense construct to be characterized. Lines 8, 17, 19, 44, 51, 53 and 60 show different degrees of reduction in the ATCase protein quantity compared with the wild type. FIG. 2 shows the Western blot analysis of the ATCase protein quantity in source leaves.

EXAMPLE 8

Phenotypic Analysis of the Transgenic Plants

Figure 3:
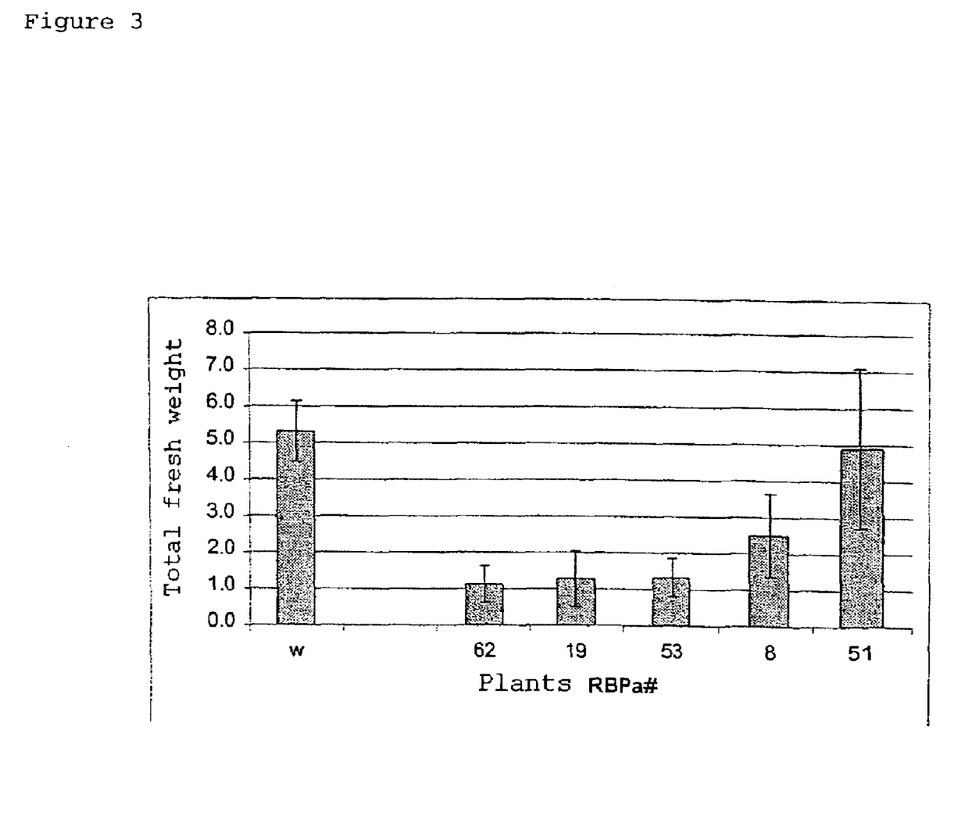
FIG. 3: Correlation between growth retardation (in the total fresh weight in grams) and the reduction in the ATCase protein quantity of the plant lines 62, 19, 53, 8 and 51 in comparison with the wild type (W).

After 5 weeks in the greenhouse, plants which carry an ATCase antisense construct and show a reduced ATCase protein quantity show different degrees of growth retardation, which leads to reduced fresh weight; see Table 1 and FIG. 3. This correlation between growth retardation and reduction in ATCase protein quantity clearly identifies ATCase for the first time as herbicide target.

TABLE 1

Analysis of the total fresh weights - mean of 5 to 8 replicates

| Plant | Mean FW [g] | Standard deviation |
|---|---|---|
| Wild type w | 5.29 | 0.83 |
| RBPa 62 | 1.12 | 0.51 |
| RBPa 19 | 1.28 | 0.77 |
| RBPa 53 | 1.32 | 0.53 |
| RBPa 8 | 2.50 | 1.14 |
| RBPa 51 | 4.90 | 2.18 |

EXAMPLE 9

ATCase Activity Measurement

The required ATCase activity can be prepared from plant tissues, for example by homogenizing leaf material while cooling with liquid nitrogen and dissolving the homogenate in extraction buffer (for example: 2 ml/100 mg fresh weight; 100 mM HEPES, pH 8.0, 2 mM EDTA, 1 mM DTE, 0.1 mM PEFA block SC, 10% glycerol).

Alternatively, a plant ATCase (preferably potato ATCase) can be generated in suitable prokaryotic (for example *E. coli*) or eukaryotic (for example yeasts, baculovirus-infected insect cells) expression systems. To this end, expression vectors must be generated which contain the ATCase cDNA. A modified length of the N-terminus of the encoded ATCase may be required to exclude any negative effects of the plastid transit peptide present at the N-terminus on the activity of the expressed protein. Suitable expression vectors for expression in *E. coli* include, for example, the types pQE—(Qiagen), pET—(Novagen), pTrc99a, pKK233-3 (Pharmacia), pBluescript II (Stratagene). To generate recombinant baculoviruses for expression in insect cells, it is possible to employ, for example, the Bac-toBac System (Gibco BRL) or the MaxBac System (Invitrogen). Vectors from the pYES series (Invitrogen) may be suitable for expression in yeast.

After the cells have been disrupted in suitable buffers and, if appropriate, after further purification steps, for example by ammonium sulfate precipitation or chromatographic methods, the ATCase activity, for example of the carbamoyl aspartate formed, can be measured analogously to described methods (Prescott & Jones, Anal. Biochem 32 (1969), 406-419; Else & Herve, Anal. Biochem 186 (1990), 219-221). To this end, an aliquot of the enzyme reaction is incubated with a solution of dye in sulfuric acid, containing antipyrines and 2,3-butanedione monoxime, in the dark for at least four hours at 40-60° C. The dye formed can be quantified photometrically at 468 nm.

Alternatively, it is possible to monitor the conversion of [$^{14}$C]carbamoyl phosphate into [$^{14}$C]carbamoyl aspartate, which is stable to acids (Lovatt and Cheng, Plant Physiology 75(1984), 511-515). This method is distinguished in particular by its sensitivity.

Particularly suitable for a high-throughput ATCase activity measurement is the method described by Wedler et al., Analytical Biochemistry 218(1994), 449-453 for detecting the resulting inorganic phosphate by reaction with purine nucleoside phosphorylase.

Applying the detection method to a microtiter plate scale allows a high-throughput search for herbicidally active ATCase activity inhibitors.

The invention claimed is:

1. A method for identifying herbicidally active inhibitors of carbamoyltransferase comprising:
functionally expressing carbamoyltransferase in an expression system;
measuring carbamoyltransferase activity from the expression system in the presence and absence of a test compound wherein, the carbamoyltransferase is encoded by a gene consisting essentially of SEQ ID NO: 1 or a derivative thereof comprising the coding region of a plant aspartate carbamoyltransferase and having at least 80% homology with SEQ ID NO:1
determining herbicidal activity of the test compound from the carbamoyltransferase activity by correlation of enzymatic activity of carbamoyltransferase with plant growth retardation; and
identifying the test compound that is an herbicidally active inhibitor of carbamoyltransferase.

2. The method of claim 1, wherein the gene is optionally linked to one or more transcriptional and/or translational control elements and the control elements facilitate expression of a translatable mRNA allowing synthesis of aspartate carbamoyltransferase in a plant.

3. An assay for identifying plant aspartate carbamoyltransferase inhibitors, which comprises:
incubating a plant aspartate carbamoyltransferase enzyme for a reaction time with a test compound, the plant aspartate carbamoyltransferase enzyme encoded by a gene sequence consisting essentially of SEQ ID NO:1 or a derivative thereof having at least 80% homology with SEQ ID NO:1;
determining the enzymatic activity of the plant aspartate carbamoyltransferase enzyme compared with the activity of the plant aspartate carbamoyltransferase enzyme in the absence of the test compound, and
identifying the test compound that is the inhibitor of the plant aspartate carbamoyltransferase enzyme.

4. The method of claim 1, wherein the expression system is selected from the group consisting of a transgenic plant, a transgenic plant tissue and a transgenic plant cell.

* * * * *

SEQUENCE LISTING

```
<160> NUMBER OF SEQ ID NOS: 6

<210> SEQ ID NO 1
<211> LENGTH: 1344
<212> TYPE: DNA
<213> ORGANISM: Solanum tuberosum
<220> FEATURE:
<221> NAME/KEY: CDS
<222> LOCATION: (106)..(1236)

<400> SEQUENCE: 1
ctcgagcagc tccaatctcc gacagaacca aacgtcatcg gaaaactctt gacgatctcc      60
gccacactgc cgccgttgtt cctctctccg gtgagtgatt tcaat atg act att tcc    117
                                                  Met Thr Ile Ser
                                                    1 gca aca ttt tct tcc cat gga aaa ata ctc atg tca cct ctt aga aag       165
Ala Thr Phe Ser Ser His Gly Lys Ile Leu Met Ser Pro Leu Arg Lys
  5                  10                  15                  20 agt gaa tgg gca aat caa cct gtg ctc tgt aaa tct gtt gaa ttg ttt       213
Ser Glu Trp Ala Asn Gln Pro Val Leu Cys Lys Ser Val Glu Leu Phe
             25                  30                  35 aaa aat gga cga aat caa tat cgt atg tca aca aat agc aac aaa ttc       261
Lys Asn Gly Arg Asn Gln Tyr Arg Met Ser Thr Asn Ser Asn Lys Phe
         40                  45                  50 caa tgc cga gca ctg gag atc gaa aat aaa tct tca act aag ttt cac       309
Gln Cys Arg Ala Leu Glu Ile Glu Asn Lys Ser Ser Thr Lys Phe His
     55                  60                  65 ctt gat gat gta att gaa tct caa caa ttt gat aga gaa act ctt agt       357
Leu Asp Asp Val Ile Glu Ser Gln Gln Phe Asp Arg Glu Thr Leu Ser
 70                  75                  80 gcg ata ttt gaa gta gca cga gag atg gag aaa atc gag aag aat tcg       405
Ala Ile Phe Glu Val Ala Arg Glu Met Glu Lys Ile Glu Lys Asn Ser
85                  90                  95                 100 att gga gga aga agc gag att ctt aag ggc tat ctt atg gct act ctg       453
Ile Gly Gly Arg Ser Glu Ile Leu Lys Gly Tyr Leu Met Ala Thr Leu
                105                 110                 115 ttt tat gaa cct tca act aga act agg ctt tca ttt gaa tct gct atg       501
Phe Tyr Glu Pro Ser Thr Arg Thr Arg Leu Ser Phe Glu Ser Ala Met
            120                 125                 130 aag cgt tta gga gga gaa gta tta aca acc gaa aat gct cgt gaa ttt       549
Lys Arg Leu Gly Gly Glu Val Leu Thr Thr Glu Asn Ala Arg Glu Phe
        135                 140                 145 tca tct gca gca aag ggg gaa aca cta gaa gat aca att aga act gtt       597
Ser Ser Ala Ala Lys Gly Glu Thr Leu Glu Asp Thr Ile Arg Thr Val
        150                 155                 160 gaa ggt tac tct gat atc att gtt atg agg cat ttc gaa agt ggt gct       645
Glu Gly Tyr Ser Asp Ile Ile Val Met Arg His Phe Glu Ser Gly Ala
165                 170                 175                 180 gct aga aga gcg gcg aca act gca tct att ccg att ata aat gca gga       693
Ala Arg Arg Ala Ala Thr Thr Ala Ser Ile Pro Ile Ile Asn Ala Gly
                185                 190                 195 gat ggt ccg gga caa cac ccg act cag gca ctt cta gat gtg tat aca       741
```

-continued

| | |
|---|---|
| Asp Gly Pro Gly Gln His Pro Thr Gln Ala Leu Leu Asp Val Tyr Thr<br>          200                    205                    210 | |
| att gaa cga gaa ata ggg aaa ctc gat ggt ata aac gtt gct ctt gtt<br>Ile Glu Arg Glu Ile Gly Lys Leu Asp Gly Ile Asn Val Ala Leu Val<br>          215                    220                    225 | 789 |
| ggt gat cta gca tac ggg agg aca gtt cgt tca ctt gct cat ttg ctt<br>Gly Asp Leu Ala Tyr Gly Arg Thr Val Arg Ser Leu Ala His Leu Leu<br>   230                    235                    240 | 837 |
| gca atg tat gaa gat gtg aaa att tac ttt gta tcc cct gat gtt gtt<br>Ala Met Tyr Glu Asp Val Lys Ile Tyr Phe Val Ser Pro Asp Val Val<br>245                    250                    255                    260 | 885 |
| aaa atg aag gat gac ata aag gat tac ttg aca tca atg ggg gtt caa<br>Lys Met Lys Asp Asp Ile Lys Asp Tyr Leu Thr Ser Met Gly Val Gln<br>                    265                    270                    275 | 933 |
| tgg gaa gaa aat gct gat ttg atc gag gtg gct tct aaa tgt gac gtg<br>Trp Glu Glu Asn Ala Asp Leu Ile Glu Val Ala Ser Lys Cys Asp Val<br>                280                    285                    290 | 981 |
| gtg tat caa act cgt att caa aga gag aga ttt gga gag agg gtt gat<br>Val Tyr Gln Thr Arg Ile Gln Arg Glu Arg Phe Gly Glu Arg Val Asp<br>          295                    300                    305 | 1029 |
| ttg tat gaa gaa gct cga ggg aag tat atc gtt gat atg agt gtc gta<br>Leu Tyr Glu Glu Ala Arg Gly Lys Tyr Ile Val Asp Met Ser Val Val<br>   310                    315                    320 | 1077 |
| aat gct atg cag aaa cat gct gta gtg atg cat cct ttg cca aga ctt<br>Asn Ala Met Gln Lys His Ala Val Val Met His Pro Leu Pro Arg Leu<br>325                    330                    335                    340 | 1125 |
| gat gag att act gtt gat gtt gat ggt gat ccg agg gct gct tat ttc<br>Asp Glu Ile Thr Val Asp Val Asp Gly Asp Pro Arg Ala Ala Tyr Phe<br>                    345                    350                    355 | 1173 |
| aga caa gct aag aat ggt ctt tac att cgg atg gcg ctt ttg aag ctt<br>Arg Gln Ala Lys Asn Gly Leu Tyr Ile Arg Met Ala Leu Leu Lys Leu<br>   360                    365                    370 | 1221 |
| cta ctc ctt ggt tgg tgaaagatgc aaactttta ttttgcgaaa tcgtgcttct<br>Leu Leu Leu Gly Trp<br>          375 | 1276 |
| tgtctggatt ctgctgttgt tgaattcaag agttttgtta acttgttta gcataaaaaa | 1336 |
| aaaaaaaa | 1344 |

```
<210> SEQ ID NO 2
<211> LENGTH: 377
<212> TYPE: PRT
<213> ORGANISM: Solanum tuberosum

<400> SEQUENCE: 2
```

Met Thr Ile Ser Ala Thr Phe Ser Ser His Gly Lys Ile Leu Met Ser
1               5                   10                  15

Pro Leu Arg Lys Ser Glu Trp Ala Asn Gln Pro Val Leu Cys Lys Ser
                20                  25                  30

Val Glu Leu Phe Lys Asn Gly Arg Asn Gln Tyr Arg Met Ser Thr Asn
            35                  40                  45

Ser Asn Lys Phe Gln Cys Arg Ala Leu Glu Ile Glu Asn Lys Ser Ser
        50                  55                  60

Thr Lys Phe His Leu Asp Asp Val Ile Glu Ser Gln Gln Phe Asp Arg
65                  70                  75                  80

Glu Thr Leu Ser Ala Ile Phe Glu Val Ala Arg Glu Met Glu Lys Ile
                85                  90                  95

Glu Lys Asn Ser Ile Gly Gly Arg Ser Glu Ile Leu Lys Gly Tyr Leu
            100                 105                 110

```
Met Ala Thr Leu Phe Tyr Glu Pro Ser Thr Arg Thr Arg Leu Ser Phe
        115                 120                 125
Glu Ser Ala Met Lys Arg Leu Gly Gly Glu Val Leu Thr Thr Glu Asn
    130                 135                 140
Ala Arg Glu Phe Ser Ser Ala Ala Lys Gly Glu Thr Leu Glu Asp Thr
145                 150                 155                 160
Ile Arg Thr Val Glu Gly Tyr Ser Asp Ile Ile Val Met Arg His Phe
                165                 170                 175
Glu Ser Gly Ala Ala Arg Arg Ala Ala Thr Thr Ala Ser Ile Pro Ile
            180                 185                 190
Ile Asn Ala Gly Asp Gly Pro Gly Gln His Pro Thr Gln Ala Leu Leu
        195                 200                 205
Asp Val Tyr Thr Ile Glu Arg Glu Ile Gly Lys Leu Asp Gly Ile Asn
    210                 215                 220
Val Ala Leu Val Gly Asp Leu Ala Tyr Gly Arg Thr Val Arg Ser Leu
225                 230                 235                 240
Ala His Leu Leu Ala Met Tyr Glu Asp Val Lys Ile Tyr Phe Val Ser
                245                 250                 255
Pro Asp Val Val Lys Met Lys Asp Asp Ile Lys Asp Tyr Leu Thr Ser
            260                 265                 270
Met Gly Val Gln Trp Glu Glu Asn Ala Asp Leu Ile Glu Val Ala Ser
        275                 280                 285
Lys Cys Asp Val Val Tyr Gln Thr Arg Ile Gln Arg Glu Arg Phe Gly
    290                 295                 300
Glu Arg Val Asp Leu Tyr Glu Glu Ala Arg Gly Lys Tyr Ile Val Asp
305                 310                 315                 320
Met Ser Val Val Asn Ala Met Gln Lys His Ala Val Val Met His Pro
                325                 330                 335
Leu Pro Arg Leu Asp Glu Ile Thr Val Asp Val Asp Gly Asp Pro Arg
            340                 345                 350
Ala Ala Tyr Phe Arg Gln Ala Lys Asn Gly Leu Tyr Ile Arg Met Ala
        355                 360                 365
Leu Leu Lys Leu Leu Leu Leu Gly Trp
    370                 375

<210> SEQ ID NO 3
<211> LENGTH: 617
<212> TYPE: DNA
<213> ORGANISM: Physcomitrella patens
<220> FEATURE:
<221> NAME/KEY: CDS
<222> LOCATION: (1)..(354)

<400> SEQUENCE: 3 ggc acg agg aag gat gat atc aaa gat cat tta acc gag tca gga gtg      48
Gly Thr Arg Lys Asp Asp Ile Lys Asp His Leu Thr Glu Ser Gly Val
  1               5                  10                  15 gat tgg gaa gaa tcc tcc gat ttg atg caa gtg gca tca aag tgt gat     96
Asp Trp Glu Glu Ser Ser Asp Leu Met Gln Val Ala Ser Lys Cys Asp
                 20                  25                  30 gta ata tac cag act cgc atc caa caa gag agg ttc ggt gat cgc atc    144
Val Ile Tyr Gln Thr Arg Ile Gln Gln Glu Arg Phe Gly Asp Arg Ile
             35                  40                  45 gac ctc tac aat gag gct cga ggg aag tac ata gtg gat acc aaa gtc    192
Asp Leu Tyr Asn Glu Ala Arg Gly Lys Tyr Ile Val Asp Thr Lys Val
         50                  55                  60
```

-continued

| | |
|---|---|
| atg gat gtg ttg ccc aag cac gga gtg gtc ctc cat ccg cta cca cgg<br>Met Asp Val Leu Pro Lys His Gly Val Val Leu His Pro Leu Pro Arg<br>65                   70                   75              80 | 240 |
| ctt gat gaa ata act gtg gag gtg gac agt gat ccc cga gct gct tat<br>Leu Asp Glu Ile Thr Val Glu Val Asp Ser Asp Pro Arg Ala Ala Tyr<br>85                   90                   95 | 288 |
| ttc cgg caa gct aag aac ggt ctt tac att cgg atg gcc ctc ttg aag<br>Phe Arg Gln Ala Lys Asn Gly Leu Tyr Ile Arg Met Ala Leu Leu Lys<br>100                   105                   110 | 336 |
| ttg ctt ctt ctc ggc tac taaggcaggt caactgtcac agtgtttgtt<br>Leu Leu Leu Leu Gly Tyr<br>115 | 384 |
| cttcgggaag tgagtgctgt gattgagata ttggattgag agtagctcag ccctctttcg | 444 |
| tgagtagtga tgatgaaatt caactgaaat tcaactaggc aagcagtaac agaaagacgt | 504 |
| agatgcaaga atttgtaaat gacaatttgg ctgtcgagtt ctgaccctca gagccacttt | 564 |
| aattgtacat acgcagttgc catagcattt aatgctaaaa aaaaaaaaaa aaa | 617 |

<210> SEQ ID NO 4
<211> LENGTH: 118
<212> TYPE: PRT
<213> ORGANISM: Physcomitrella patens

<400> SEQUENCE: 4

Gly Thr Arg Lys Asp Asp Ile Lys Asp His Leu Thr Glu Ser Gly Val
1               5                 10               15

Asp Trp Glu Glu Ser Ser Asp Leu Met Gln Val Ala Ser Lys Cys Asp
            20                 25               30

Val Ile Tyr Gln Thr Arg Ile Gln Gln Glu Arg Phe Gly Asp Arg Ile
         35                 40               45

Asp Leu Tyr Asn Glu Ala Arg Gly Lys Tyr Ile Val Asp Thr Lys Val
  50               55               60

Met Asp Val Leu Pro Lys His Gly Val Val Leu His Pro Leu Pro Arg
65                   70                   75              80

Leu Asp Glu Ile Thr Val Glu Val Asp Ser Asp Pro Arg Ala Ala Tyr
         85                 90               95

Phe Arg Gln Ala Lys Asn Gly Leu Tyr Ile Arg Met Ala Leu Leu Lys
        100               105             110

Leu Leu Leu Leu Gly Tyr
        115

<210> SEQ ID NO 5
<211> LENGTH: 1251
<212> TYPE: DNA
<213> ORGANISM: Physcomitrella patens
<220> FEATURE:
<221> NAME/KEY: CDS
<222> LOCATION: (1)..(933)
<223> OTHER INFORMATION: c_pp015013185r

<400> SEQUENCE: 5

| | |
|---|---|
| agg ttt cca tta cag gat gta ctg gaa gcg cag cag ttc gac agg aaa<br>Arg Phe Pro Leu Gln Asp Val Leu Glu Ala Gln Gln Phe Asp Arg Lys<br>1               5                 10               15 | 48 |
| ctt ctg aac tct atc ttt gag gtg gca agg gaa atg gaa gac ata gag<br>Leu Leu Asn Ser Ile Phe Glu Val Ala Arg Glu Met Glu Asp Ile Glu<br>            20                 25               30 | 96 |
| agg gat gct gct gga tcg gag ctg ctg aag gga ttc tta atg gct acc<br>Arg Asp Ala Ala Gly Ser Glu Leu Leu Lys Gly Phe Leu Met Ala Thr<br>         35                 40               45 | 144 |

```
ctg ttt tac gaa cct tcc act cgt act agg ctt tcg ttc gaa tcc gct      192
Leu Phe Tyr Glu Pro Ser Thr Arg Thr Arg Leu Ser Phe Glu Ser Ala
 50                  55                  60 atg aag agg ctg ggt gga gaa gtt ttg acg act gaa aat gct cgt gaa      240
Met Lys Arg Leu Gly Gly Glu Val Leu Thr Thr Glu Asn Ala Arg Glu
 65                  70                  75                  80 ttt tct tca gct gcc aag ggc gag acc ctg gaa gat acc att aga aca      288
Phe Ser Ser Ala Ala Lys Gly Glu Thr Leu Glu Asp Thr Ile Arg Thr
                 85                  90                  95 gtc gag ggc tat tcg gat att att gtg ctc agg cac ttc gag agt ggg      336
Val Glu Gly Tyr Ser Asp Ile Ile Val Leu Arg His Phe Glu Ser Gly
            100                 105                 110 gca gcc aag aag gct gcc aat aca gcg aac att cct atc ata aat gca      384
Ala Ala Lys Lys Ala Ala Asn Thr Ala Asn Ile Pro Ile Ile Asn Ala
                115                 120                 125 gga gat ggt cct ggt cag cat cct aca cag gcg ctg ctc gac atg tat      432
Gly Asp Gly Pro Gly Gln His Pro Thr Gln Ala Leu Leu Asp Met Tyr
130                 135                 140 aca ata aaa cga gag att ggc cat ctg gat aac ata aga gtg ggg ttg      480
Thr Ile Lys Arg Glu Ile Gly His Leu Asp Asn Ile Arg Val Gly Leu
145                 150                 155                 160 gtg ggt gat tta gct aat ggg cga act gta cga tca ttg gct tat ctg      528
Val Gly Asp Leu Ala Asn Gly Arg Thr Val Arg Ser Leu Ala Tyr Leu
                165                 170                 175 ctt gcg aag tac gat gga gtc aaa att tac ttt gtt gct cct gat gtg      576
Leu Ala Lys Tyr Asp Gly Val Lys Ile Tyr Phe Val Ala Pro Asp Val
            180                 185                 190 gtc aag atg aag gat gat atc aag gac cac ctg act gat tca gga gtc      624
Val Lys Met Lys Asp Asp Ile Lys Asp His Leu Thr Asp Ser Gly Val
                195                 200                 205 gat tgg gaa gaa tcc act gac ctg atg gaa gtg gca tca aag tgt gat      672
Asp Trp Glu Glu Ser Thr Asp Leu Met Glu Val Ala Ser Lys Cys Asp
210                 215                 220 gtg ata tac caa act cgt atc caa cgt gag agg ttt ggt gac cgc att      720
Val Ile Tyr Gln Thr Arg Ile Gln Arg Glu Arg Phe Gly Asp Arg Ile
225                 230                 235                 240 gac ttg tac aat gcg gct cgt gga aag tat att gtg gat acc aag gtt      768
Asp Leu Tyr Asn Ala Ala Arg Gly Lys Tyr Ile Val Asp Thr Lys Val
                245                 250                 255 atg aat gtg tta ccc aag cat gcg gtg gtt ctc cat cct cta cca cgt      816
Met Asn Val Leu Pro Lys His Ala Val Val Leu His Pro Leu Pro Arg
            260                 265                 270 ctc gat gag ata act gtg gaa gtg gac agt gat ccc cga gct gct tac      864
Leu Asp Glu Ile Thr Val Glu Val Asp Ser Asp Pro Arg Ala Ala Tyr
                275                 280                 285 ttc cgt caa gct aag aat ggt ctg cac att cgg atg gcc tta ctc aag      912
Phe Arg Gln Ala Lys Asn Gly Leu His Ile Arg Met Ala Leu Leu Lys
290                 295                 300 ctg ctt ctt ctt ggc tac taa gggagaagct catgtagcaa ttttggtgca         963
Leu Leu Leu Leu Gly Tyr
305                 310 caggattagg ctgctgagtg ttgcgcatag gattgagagt agtgaacagg gtttcgtgag    1023
gaggtcacat tgaatataaa ttcaatcgga gaaggatttt ctgtaaactg acaaaagcaa    1083
cctagtgcaa aagttcctac gaataatttt tttgttatgt tctgactcca gaactttctg    1143
aaattgtaca tagagagctg cctttcattc aatgtcgcaa acaactgggc acctcctaga    1203
aattggcggc tttgctaaaa aaaaaaaaaa aaaaaaaaaa aaaaaaaa                 1251
```

```
<210> SEQ ID NO 6
<211> LENGTH: 310
<212> TYPE: PRT
<213> ORGANISM: Physcomitrella patens

<400> SEQUENCE: 6

Arg Phe Pro Leu Gln Asp Val Leu Glu Ala Gln Gln Phe Asp Arg Lys
  1               5                  10                  15

Leu Leu Asn Ser Ile Phe Glu Val Ala Arg Glu Met Glu Asp Ile Glu
             20                  25                  30

Arg Asp Ala Ala Gly Ser Glu Leu Leu Lys Gly Phe Leu Met Ala Thr
         35                  40                  45

Leu Phe Tyr Glu Pro Ser Thr Arg Thr Arg Leu Ser Phe Glu Ser Ala
     50                  55                  60

Met Lys Arg Leu Gly Gly Glu Val Leu Thr Thr Glu Asn Ala Arg Glu
 65                  70                  75                  80

Phe Ser Ser Ala Ala Lys Gly Glu Thr Leu Glu Asp Thr Ile Arg Thr
                 85                  90                  95

Val Glu Gly Tyr Ser Asp Ile Ile Val Leu Arg His Phe Glu Ser Gly
            100                 105                 110

Ala Ala Lys Lys Ala Ala Asn Thr Ala Asn Ile Pro Ile Ile Asn Ala
        115                 120                 125

Gly Asp Gly Pro Gly Gln His Pro Thr Gln Ala Leu Leu Asp Met Tyr
    130                 135                 140

Thr Ile Lys Arg Glu Ile Gly His Leu Asp Asn Ile Arg Val Gly Leu
145                 150                 155                 160

Val Gly Asp Leu Ala Asn Gly Arg Thr Val Arg Ser Leu Ala Tyr Leu
                165                 170                 175

Leu Ala Lys Tyr Asp Gly Val Lys Ile Tyr Phe Val Ala Pro Asp Val
            180                 185                 190

Val Lys Met Lys Asp Asp Ile Lys Asp His Leu Thr Asp Ser Gly Val
        195                 200                 205

Asp Trp Glu Glu Ser Thr Asp Leu Met Glu Val Ala Ser Lys Cys Asp
    210                 215                 220

Val Ile Tyr Gln Thr Arg Ile Gln Arg Glu Arg Phe Gly Asp Arg Ile
225                 230                 235                 240

Asp Leu Tyr Asn Ala Ala Arg Gly Lys Tyr Ile Val Asp Thr Lys Val
                245                 250                 255

Met Asn Val Leu Pro Lys His Ala Val Val Leu His Pro Leu Pro Arg
            260                 265                 270

Leu Asp Glu Ile Thr Val Glu Val Asp Ser Asp Pro Arg Ala Ala Tyr
        275                 280                 285

Phe Arg Gln Ala Lys Asn Gly Leu His Ile Arg Met Ala Leu Leu Lys
    290                 295                 300

Leu Leu Leu Leu Gly Tyr
305                 310
```